US012491379B2

(12) United States Patent
Voet et al.

(10) Patent No.: US 12,491,379 B2
(45) Date of Patent: Dec. 9, 2025

(54) METHOD AND SYSTEM FOR TREATMENT PLANNING

(71) Applicant: Elekta, Inc., Atlanta, GA (US)

(72) Inventors: Peter Voet, Atlanta, GA (US); Chunhua Men, Atlanta, GA (US); Spencer Marshall, Brandon, FL (US)

(73) Assignee: Elekta, Inc., Atlanta, GA (US)

( * ) Notice: Subject to any disclaimer, the term of this patent is extended or adjusted under 35 U.S.C. 154(b) by 308 days.

(21) Appl. No.: 18/315,978

(22) Filed: May 11, 2023

(65) Prior Publication Data

US 2024/0374927 A1 Nov. 14, 2024

(51) Int. Cl.
*G16H 20/40* (2018.01)
*A61N 5/10* (2006.01)

(52) U.S. Cl.
CPC ........... *A61N 5/1031* (2013.01); *G16H 20/40* (2018.01); *A61N 2005/1074* (2013.01)

(58) Field of Classification Search
CPC ......... A61N 5/1031; A61N 2005/1074; G16H 20/40
See application file for complete search history.

(56) References Cited

U.S. PATENT DOCUMENTS

| | | | |
|---|---|---|---|
| 6,064,203 | A | 5/2000 | Bottomley |
| 6,963,771 | B2 | 11/2005 | Scarantino et al. |
| 7,317,192 | B2 | 1/2008 | Ma |
| 8,492,735 | B2 | 7/2013 | Brand |
| 9,884,206 | B2 | 2/2018 | Schulte et al. |
| 10,737,114 | B2 | 8/2020 | Gattiker et al. |
| 10,835,760 | B2 | 11/2020 | Kuusela et al. |
| 2015/0202464 | A1 | 7/2015 | Brand et al. |
| 2018/0154177 | A1 | 6/2018 | Bzdusek et al. |
| 2018/0304099 | A1 | 10/2018 | Li et al. |
| 2019/0038916 | A1 | 2/2019 | Ranganathan et al. |
| 2021/0138267 | A1 | 5/2021 | Nord et al. |
| 2021/0316157 | A1 | 10/2021 | Lynch et al. |
| 2021/0379404 | A1 | 12/2021 | Basiri et al. |

FOREIGN PATENT DOCUMENTS

| | | |
|---|---|---|
| EP | 3681600 | 7/2020 |

OTHER PUBLICATIONS

"European Application No. 24175408.4, Extended Search Report dated Sep. 4, 2024", (Sep. 4, 2024), 9 pgs.

(Continued)

*Primary Examiner* — Mark R Gaworecki
(74) *Attorney, Agent, or Firm* — Schwegman Lundberg & Woessner, P.A.

(57) ABSTRACT

A computer-implemented method may be provided to aid in radiation treatment planning, the method comprising: receiving treatment plan parameters including a reference dose value for a target region of a patient and a defined dose value for a surrounding region; determining whether the defined dose value for the surrounding region exceeds a threshold; and responsive to determining that the defined dose value for the surrounding region does not exceed the threshold, modifying the defined dose value for the surrounding region, and applying an optimization procedure to a treatment plan for radiation treatment of the patient with the modified dose value for the surrounding region.

19 Claims, 6 Drawing Sheets

(56) References Cited

OTHER PUBLICATIONS

Hong, Theodore S., "Multicriteria optimization in intensity-modulated radiation therapy treatment planning for locally advanced cancer of the pancreatic head", International Journal of Radiation Oncology* Biology* Physics 72.4, (2008), 1208-1214.
Mashayekhi, Maryam, "Artificial intelligence guided physician directive improves head and neck planning quality and practice Uniformity: A prospective study", Clinical and Translational Radiation Oncology 40, (2023), 100616.
Elekta AB, "", Monaco Training Guide, Document ID: LTGMON0530, (2017), 1313 pgs.

METHOD AND SYSTEM FOR TREATMENT PLANNING

TECHNICAL FIELD

The present disclosure relates to methods and systems for treatment planning. More specifically, the present disclosure relates to a computer-implemented method for radiation treatment planning, and data processing apparatuses, computer programs, and non-transitory computer-readable storage mediums configured to execute methods for radiation treatment planning.

BACKGROUND

Radiation therapy or radiotherapy may be described as the use of ionising radiation to damage or destroy unhealthy cells in both humans and animals. The ionising radiation may be directed to tumours on the surface of the skin or deep inside the body. Common forms of ionising radiation include X-rays and charged particles. An example of a radiotherapy technique is Gamma Knife®. where a patient is irradiated using a number of lower-intensity gamma rays that converge with higher intensity and high precision at a targeted region (e.g., a tumour). Another example of radiotherapy comprises using a linear accelerator ("linac"), whereby a targeted region is irradiated by high-energy particles (e.g., electrons, high-energy photons, and the like). In another example, radiotherapy may be provided using a heavy charged particle accelerator (e.g., protons, carbon ions, and the like).

The placement and dose of the radiation beam may be accurately controlled to provide a prescribed dose of radiation to the target region (e.g., the tumour) and to reduce damage to surrounding healthy tissue (known as organs at risk or OARs). An aspect of treatment planning concerns determining suitable characteristics of radiation to be delivered to produce a safe and effective dose. Characteristics of radiation relate to, for example, a fluence pattern or distribution. The fluence pattern may be dependent on beam arrangements, energies, and field sizes, which are in turn related to controllable parameters (which are optimizable). By determining suitable values for those parameters, a suitable fluence pattern may be obtained. A treatment plan may be determined by a treatment planning system.

A radiation therapy treatment plan (treatment plan, or simply plan) may be established using an optimization procedure to determine a set of optimum parameter values or optimum variable values that are expected to deliver a suitable dose. The optimization procedure may be based on clinical and dosimetric objectives and constraints. Examples of clinical and dosimetric objectives and constraints include maximum, minimum, and mean doses to target regions and surrounding regions (e.g., tumours and critical organs). Clinical and dosimetric objectives and constraints may be referred to as treatment planning objectives. Optimization is usually carried out with respect to one or more treatment plan parameters to reduce beam-on time, improve dose uniformity, etc.

A treatment planning procedure may include using an image (two- or three-dimensional) of the patient to identify a target region and to identify critical organs near the target region. The target region (or area to be treated, e.g., a planned target volume, PTV), and surrounding region (or Organs at Risk, OARs) may be identified using segmentation. After segmentation, a dose plan may be created for the patient indicating the desirable amount of radiation to be received by the target region and/or the surrounding region.

The target region may have an irregular volume and may be distinctive in terms of its size, shape, and position.

In a practical example, multiple anatomical structures (target regions and/or surrounding regions) may be present. For example, in a head and neck treatment, there may be over 20 anatomical structures. For each structure, compliance with various treatment-planning objectives may be desired. Structures and their objectives may be assigned different priorities in order to achieve a clinically acceptable plan. Determining a treatment plan to meet the various objectives is time-consuming and complex.

Creation of a radiation treatment plan is typically a time-consuming process where a planner may try to comply with various treatment objectives or constraints—considering their individual importance—to produce a radiation treatment plan that is clinically acceptable. Common issues faced when creating radiation treatment plans that involve optimization procedures include lengthy optimization times and high computational burdens required to achieve safe and satisfactory results. These processes often involve trial-and-error on the part of the user (e.g., a treatment planner, dosimetrist, clinician, or health care worker), may be time-consuming, and are further complicated with the addition of further objectives and constraints.

Therefore, it is desirable to reduce the planning time with an improved radiotherapy treatment planning workflow.

SUMMARY

According to an aspect, there is provided a computer-implemented method for radiation treatment planning. The method comprises receiving treatment plan parameters including a reference dose value for a target region of a patient and a defined dose value for a surrounding region. The method further comprises determining whether the defined dose value for the surrounding region exceeds a threshold. The method further comprises, responsive to determining that the defined dose value for the surrounding region does not exceed the threshold, modifying the defined dose value for the surrounding region, and applying an optimization procedure to a treatment plan for radiation treatment of the patient with the modified dose value for the surrounding region.

The reference dose value and the defined dose value are reference objectives, representative of goals to be achieved by the radiation treatment. The dose values are typically provided in SI units of gray (Gy). The dose values may be mean dose values for the entire region in question. The dose values may be dose-based (e.g., indicating an absorbed dose to be delivered to the target region or surrounding region) or may be volume-based (e.g., indicating an absorbed dose to be delivered to a specified volume of the target region or surrounding region). The dose values may be input by a user or may be otherwise received by the computer implementing the method.

The surrounding region (or neighbouring region, or OAR) need not be in physical contact with the target region, rather the surrounding region may include regions of the patient other than the target region in which the user wishes to limit or otherwise control the absorbed dose.

The threshold may be a fixed value or may be a variable value, which for example varies as a function of another parameter. In one example, the threshold may be a fraction (e.g., 50%) of the reference dose value for the target region of the patient.

In the event that the defined dose value for the surrounding region does not exceed the threshold, the method modifies the defined dose value for the surrounding region. For instance, if a fixed threshold of 10 Gy is used and the defined dose is 5 Gy, the method may increase the defined dose. In one example, the method may increase the defined dose to correspond to the threshold value. In the event that the defined dose value already exceeds the threshold, the method may proceed to optimization without modification of the defined dose value.

The optimization procedure seeks to determine parameters that are expected to result in achieved doses that are as close to the modified dose value for the surrounding region and the reference dose value for the target region as practicable (that is, in respect of any processing and/or time constraints).

Broadly, the method for radiation treatment planning addresses a technical problem arising in the field of radiotherapy treatment planning, namely, how to improve generation of a treatment plan. The method may improve the accuracy of the generated treatment plan and the speed of generation. The method also automates the generation of a treatment plan. A typical user may—understandably—ask for unrealistically low dose values for surrounding regions when planning a radiation treatment procedure. For example, when the reference dose value for a target region (e.g., a cancerous mass) is 60 Gy (typical dose values for treatment of solid epithelial tumours range from 60 to 80 Gy), the user may set the defined dose value for an overlapping OAR to a value as low as 5 Gy, so as to determine a radiation treatment plan that has minimal negative effect of the OAR. In this example, the 5 Gy goal is so low that the optimization procedure is highly inefficient and will typically result in suboptimal treatment plans. The inventors have come to the realisation that the automated modification of unrealistic define dose values routinely improves speed of optimization and accuracy of generated treatment plans.

Further, the automated modification of unrealistic define dose values improves robustness of optimization; the optimization problem (that is, the parameters the optimization procedure seeks to optimize with respect to objectives and/or constraints) remains realistic and feasible at all times. Some techniques, which aim for an unrealistic low dose from the start of the optimization, severely limit the solution space. This means that, potentially, the only focus of these techniques may be on such unrealistic goals. Aiming for a less aggressive goal and gradually lowering the goal based on feasibility of solution allows the optimizer to remain in a "sane" condition. In other words, the techniques disclosed herein enable optimization to consider the entire solution space, all goals, and all constraints without the optimization sticking in a less favourable situation or optimization space.

Without the techniques disclosed herein, other techniques provide suboptimal plans, typically involving slow optimization procedures (as the optimizer is required to run longer to arrive at some acceptable plan). Unreasonable starting values often cause extremely large cost function values that computer (programming language) cannot efficiently handle (e.g., causing "not-a-number" errors)

In automating the procedure, the user is not burdened with selection of defined dose values for surrounding regions, which may vary significantly between patients with differing anatomies. The user may not know upfront if, for the particular patient in question, the defined dose value is realistic or not. The method changes the input to a more reasonable starting value.

Optionally, the optimization procedure comprises determining a dose distribution indicating expected dosage in the target region and in the surrounding region. This determination may be based on the reference dose value for the target region and the modified dose value for the surrounding region (that is, the defined dose value for the surrounding region following modification responsive to determination that the value is below the threshold).

Optionally, in response to a determination that the dose distribution matches the modified dose value for the surrounding region, the optimization procedure comprises adjusting the modified dose value towards the defined dose value. This may occur during an iterative optimization procedure, where the modified dose value is iteratively (further) modified during each pass. The matching of dose distribution (or aspects thereof, e.g., the expected dosage in the target region or in the surrounding region) need not be exact, rather the two quantities may be considered to match if the two quantities are roughly equal, for instance within a 1% tolerance or within an absolute absorbance tolerance, such as within 0.1 Gy. The optimization procedure then repeatedly determines the dose distribution (indicating expected dosage in the target region and in the surrounding region) until a stopping criterion for the dosage in the surrounding region is reached. The stopping criterion may, for instance, be a convergence criterion, for example where changes in the obtained doses in the surrounding region between consecutive iterations are less than a defined value, and/or may be a time-based criterion, for example where a defined number of repetitions of the optimization procedure are performed.

In this way, the optimization procedure seeks to formulate a treatment plan capable of achieving the constraint/objective defined dose value for the surrounding region in a "gentler" manner than optimization procedures without iterative modification of dose values. Using a stepwise, automated approach, the solution space for the optimization procedure remains feasibly computationally assessable throughout the optimization procedure.

Optionally, the modified dose value may be adjusted towards the defined dose value during the optimization procedure by a fixed value. Alternatively, the modified dose value may be adjusted by a variable value. For instance, the value may be a percentage of the difference between the defined dose value and the current modified dose value.

Optionally, the reference dose value for the target region may be a minimum dose value for the treatment of the target region. The defined dose value for the surrounding region may be a maximum dose value for the surrounding region during treatment of the target region. These values may be selected by a skilled practitioner in view of the particular tissues or organs in the vicinity of the radiation treatment.

Optionally, the optimization procedure may seek to minimize a cost function. The cost function may be representative of dose excess value in the surrounding region and/or the target region. That is, the optimization procedure may consider a function that maps values of optimizable parameters onto some number, which represents the "cost" of the radiation treatment on at least the target region and the surrounding region. The cost may be referred to as a loss. Alternatively, the optimization procedure may seek instead to maximise an objective function (or reward function, profit function, etc.).

Optionally, the cost function may be a maximum dose cost function, which is effectively a hard barrier that may be applied to target regions or surrounding regions. The maximum dose cost function involves a penalty that takes effect whenever the dose value in simulated regions (e.g., pixels, or voxels) cross a maximum dose threshold. The cost function takes as input maximum dose.

Optionally, the cost function may be a serial cost function, which is generally used with serial surrounding regions. Serial anatomical structures are those where high doses are harmful even if limited to small volumes. Examples include the spinal cord and bowel. This cost function applies large penalties for hot spots even if they are small in volume. The cost function takes as input an equivalent uniform dose and a power law exponent.

Optionally, the optimization procedure may seek to minimize the cost function with respect to one or more optimizable parameters so as to arrive at a radiation treatment plan capable of treating a patient with clinically acceptable accuracy and expected efficacy.

The optimizable parameters may include a dose excess value, which is an amount of dosage violation that is considered acceptable. The optimizable parameters may include weights of beamlets; in a radiation beam may be divided into a number of beamlets where the contribution, at (hypothetical) unit fluence, may be determined. The weight of a beamlet is then a scaling factor, by which the unit fluence of the beamlet may be scaled to arrive at another fluence value. The optimizable parameters may include beam (or beamlet) angles, which may be the angle of a beam—relative to a reference point, such as a radiation head of a radiotherapy system, towards a target region. The optimizable parameters may include dose-histogram-volume information, which provides information related to the cumulative dose per volume fraction of target region or surrounding region. A “fraction” may be derived using a process of “fractioning,” whereby a sequence of radiation therapy deliveries is provided over a predetermined period of time (e.g., 45 fractions), with each therapy delivery including a specified fraction of a total prescribed dose. The optimizable parameters may include a number of radiation beams. The optimizable parameters may include a dose per radiation beam. The optimizable parameters may include segment or control point shapes. The optimizable parameters may include segment or control point weights. The optimization procedure may adapt any or all of the optimizable parameters.

Optionally, the method for radiation treatment planning may consider multiple surrounding regions. That is, the treatment plan parameters may include defined dose values for a plurality of surrounding regions. The method may then determine whether each defined dose value for the corresponding surrounding region exceeds a corresponding threshold, and then modify each corresponding defined dose value accordingly. In this way, the optimization procedure may be repeatedly applied in respect of multiple surrounding regions of the patients. Of course, the thresholds may be the same for each surrounding region or may differ for each surrounding region (e.g., in view of differing acceptable levels of absorbed dose rates between different tissues).

Optionally, the method for radiation treatment planning may consider multiple target regions. That is, the treatment plan parameters may include reference dose values for a plurality of target regions. The method may then determine whether the defined dose value for the surrounding region exceeds a corresponding threshold in view of each reference dose value, and the defined dose value may be modified accordingly. In this way, the optimization procedure may be repeatedly applied in respect of multiple target regions of the patients. Of course, the threshold for the surrounding region may be the same for each target region. Of course, the method may consider multiple surrounding regions and multiple target regions. Both surrounding regions and target regions may be allocated priority values, indicating the region’s importance. For example, the method may place greater emphasis on achieving the defined dose value or reference dose value for higher prioritised regions than for lower prioritised regions. In one example, the optimization procedure may be initially performed on high priority regions before turning to low priority regions.

Optionally, the threshold (for defined dose value) may be variable, dependent on the cost function used in optimization. Different cost functions may be more or less susceptible to computational inefficiencies when faced with unrealistically low defined dose values; in selecting a tailored threshold for each corresponding cost function, potential inefficiencies are avoided.

Optionally, the treatment plan parameters may include images of the patient, including the target region and the surrounding region. Some methods may be configured to process or pre-process image data. For example, some methods may convert received image data into a particular format, size, or resolution, suitable for radiation treatment planning optimization, and/or may process image data to perform segmentation, defining target region and surrounding region.

Optionally, the method for radiation treatment planning may include accepting user input into a graphical user interface, where the user input comprises the dose value for the target region and the defined dose value for the surrounding region.

Optionally, the method for radiation treatment planning may include outputting parameter values corresponding to the treatment plan. The parameter values may comprise any or all of the following: number of beams, beam angles, a dose per beam, beamlet weights, segment or control point shapes, segment or control point weights, dose-volume histogram information, a dose excess value. In this way, the method may output parameter values (and, of course, configuration settings) for a radiotherapy system, so as to be able to deliver the radiation plan to the patient.

Embodiments of another aspect include a data processing apparatus comprising a memory storing computer-readable instructions and a processor. The processor (or controller circuitry) is configured to execute the instructions to carry out the computer-implemented method for radiation treatment planning.

Embodiments of another aspect include a computer program comprising instructions, which, when executed by computer, causes the compute to execute the computer-implemented method for radiation treatment planning.

Embodiments of another aspect include a non-transitory computer-readable storage medium comprising instructions, which, when executed by a computer, causes the compute to execute the computer-implemented method for radiation treatment planning.

The systems and methods described herein may be implemented in digital electronic circuitry, or in computer hardware, firmware, software, or in combinations thereof. The systems and methods may further be implemented as a computer program or a computer program product, i.e., a computer program tangibly embodied in a non-transitory information carrier, e.g., in a machine-readable storage device or in a propagated signal, for execution by, or to control the operation of, one or more hardware modules. A computer program may be in the form of a stand-alone program, a computer program portion, or more than one computer program, and may be written in any form of programming language, including compiled or interpreted languages, and it may be deployed in any form, including as a stand-alone program or as a module, component, subroutine, or other unit suitable for use in a data processing environment.

The present disclosure is described in terms of particular embodiments or examples. Other embodiments are within the scope of the following claims. For example, the steps of the present disclosure may be performed in a different order and still achieve desirable results.

BRIEF DESCRIPTION OF THE DRAWINGS

Reference is made, by way of example only, to the accompanying drawings in which.

DETAILED DESCRIPTION

Treatment planning typically involves performing an optimization procedure to optimize a number of parameters, the purpose being to provide a sufficiently high dose to the target region (or planned target volume, PTV) while reducing the dose to the surrounding healthy tissue. By balancing the different treatment-planning objectives, for example by prioritising treatment-planning objectives that relate to the dose coverage at the target region and then treatment planning that relate to sparing surrounding regions, a clinically suitable plan may be obtained. However, a user may ask for unrealistically low defined dose values in surrounding regions, which negatively impacts the optimization procedures and—in turn—negatively effects the treatment planning process.

Figure 1:
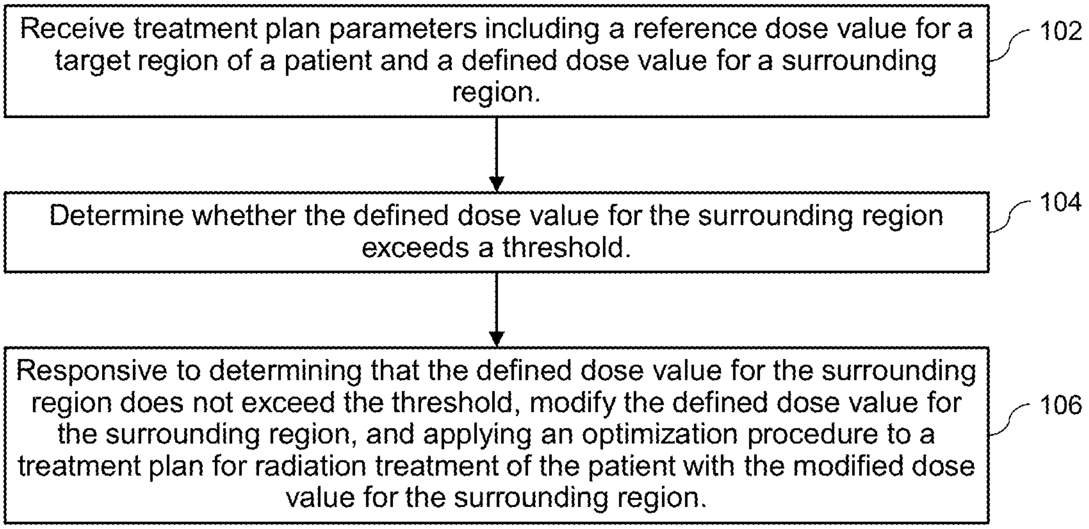
FIG. 1 is a flow chart of a general method for radiation treatment planning.

FIG. 1 shows a general method for radiation treatment planning, which addresses unrealistic defined dose values. At step 102, a computer receives treatment plan parameters including a reference dose value for a target region of a patient and a defined dose value for a surrounding region. At step 104, the computer determines whether the defined dose value for the surrounding region exceeds a threshold. At step 106, responsive to determining that the defined dose value for the surrounding region does not exceed the threshold, the computer modifies the defined dose value for the surrounding region, and applying an optimization procedure to a treatment plan for radiation treatment of the patient with the modified dose value for the surrounding region.

Any optimization procedure that accepts treatment plan parameters including a reference dose value for a target region and a defined dose value for a surrounding region, which seeks to determine optimum (as far as practicable) parameter values is suitable for incorporation into methods according to embodiments. For instance, the method may implement the optimization procedure described in European patent application publication EP3681600A1.

Adherence to objectives and constraints involved in optimization procedures may be quantified using cost functions, where a cost function output is a measure of the difference between a dose achieved by the treatment plan (e.g., the dose in a given region) and a reference dose (e.g., a maximum acceptable dose in that region).

Figure 2A:
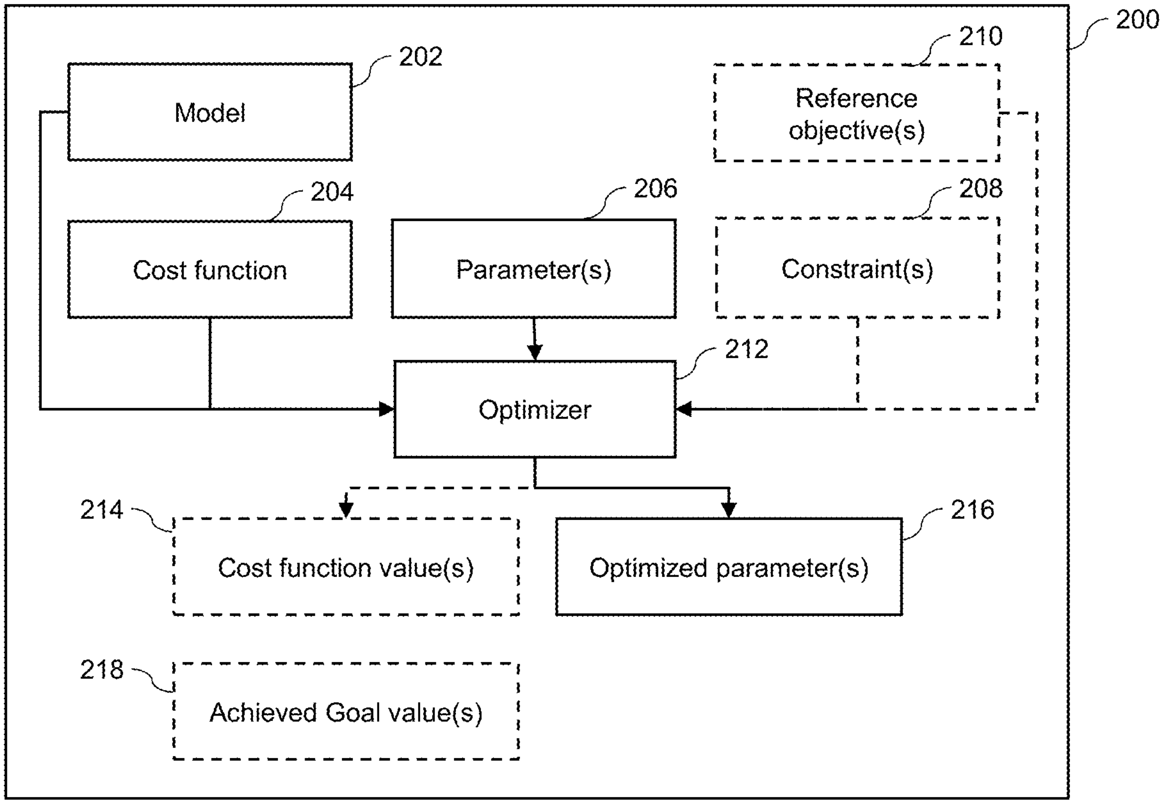
FIG. 2A is an example optimization procedure.

FIG. 2 shows a block diagram of an example optimization procedure. The optimization procedure is applicable to the optimization of a set of parameters (i.e., one or more parameters) for a radiotherapy system. The one or more parameters may be referred to as optimizable parameters, or as decision variables. Examples of optimizable parameters comprise parameters that relate to characteristics of radiation to be delivered by the radiotherapy system, such as radiation beam angles, radiation intensity level at each angle, etc. Optimization is typically carried out with respect to one or more parameters to reduce beam-on time, improve dose uniformity, etc. An example of a radiotherapy system will be described below.

The optimization module 200 may comprise an optimizer 212. Given an anatomical model 204 and one or more parameters 206, the purpose of the optimizer 212 is to provide a set of optimized parameters 216 that minimise cost function 204. The optimizer comprises at least one optimization algorithm. Examples of optimization algorithms include a simplex algorithm, a gradient-based algorithm, or an interior point algorithm, etc., or a combination thereof. Other optimization algorithms are also possible. Examples of optimization are provided in Monaco® Training Guide, Document ID: LTGMON0530 (Elekta AB).

The cost function value 214 is value of the cost function 204 when evaluated with the set of optimized parameters 216. The cost function value 214 is calculated by the optimizer 212 during optimization. The cost function value 214 may be referred to as a penalty. Optionally, the cost function value 214 is output by the optimizer 212.

The model 202 is a representation of the physical problem. The model 202 may correspond to an anatomical structure or regions thereof. The model 202 may comprise a target region (or PTV) and a surrounding region of healthy tissue or otherwise critical structures (known as organs at risk or OARs). These regions may be determined and/or defined during a process known as segmentation, performed on a two- or three-dimensional image or model of the anatomical structure. These regions may be in the form of shell structures, which are structures generated to tune the dose delivered to the tissue surrounding the target, and they may be used to control dose distribution conformality. The dose distribution may be determined by pencil beam algorithms, convolution based algorithms, and/or Monte Carlo (MC) based algorithms. Further details of how the dose may be determined are provided in Monaco® Training Guide, Document ID: LTGMON0530 (Elekta AB).

The one or more parameters 206 may be optimizable parameters (also referred to as decision variables) for which the optimizer 212 attempts to find optimum values. The one or more parameters 206 may be initialised to a predetermined value. In an example, for intensity-modulated radiation therapy, IMRT, the parameters 206 are the weight of beamlets, the parameters 206 may be initialised to a predetermined weight. The weight of a beamlet may map to an actual beamlet intensity during radiation treatment, where the intensity may be altered, for instance, by varying an aperture size or pulse time. Alternatively, the parameters 206 may be initialised to values determined in a previous step. For example, when a further optimization procedure (or pass) is performed, the parameters may be initialised to values determined in a previous optimization procedure (or pass).

The cost function 204 is a mathematical formulation that relates the parameters 206 and the model 202. The cost function 204 may be referred to as an objective function. The cost function 204 relates the dose distribution in the model 202 to a single value (the cost function value 214). For example, the cost function value 214 defines a penalty for violating objectives and/or constraints. The penalty may be evaluated by the optimizer 212 during optimization. Optionally, in constrained optimization, only objectives contribute to the cost function (that is, a constraint remains "fixed", and the optimization procedure does not permit the constraint to be violated, because. a violation of the constraint 208 simply results in a rejection of the treatment plan).

The constraints 208 comprise one or more conditions that the optimized parameters 216 must satisfy. The constraints may include hard constraints (conditions that the parameters 206 are required to satisfy). Constraints restrict the set of solutions that are obtainable. Constraints are used to define what is physically or clinically acceptable rather than what is mathematically possible. For example, for IMRT, a hard constraint may be that the weights of the beamlets must be non-negative (since a negative beamlet weight is not possible). Note that the constraint 208 is an optional feature.

The reference objective 210 comprises a goal that the optimizer 212 attempts to achieve. For example, in IMRT, the reference objective may relate to a dose-based objective and/or a volume-based objective. A dose-based objective may comprise a dose value (in Gy), for instance a maximum, minimum, or mean dose for a given region. For example, a dose-based objective may set out that dose absorbed in a 10 $mm^3$ volume should not exceed 25 Gy. A volume-based objective may comprise a relative volume (a fraction or a percentage of a volume) or an absolute volume (or, in 2-dimensional cases, an absolute area). For instance, a volume-based objective may set out that the dose absorbed in 50% of the volume of an OAR should not exceed 5 Gy. The volume (or area) may be defined in terms of physical dimensions (e.g., in $mm^2$, $cm^2$, $mm^3$, $cm^3$). Additionally, the reference objective 210 may comprise an indication of a cost function 204 to be used. Further, the reference objective 210 may comprise an indication of an anatomical structure to which the goal to be achieved is applicable. The optimizer 212 will then determine optimized parameters 216 that result in an achieved goal value 218 that is close to the reference objective 210. The reference objective may be referred to as a treatment-planning objective. Note that the reference objective 210 is an optional feature.

The reference objective 210 may therefore be an anatomy-specific function that establishes the dose and/or biological response goal. Constraints 208 are anatomy-specific functions that must be met to enable optimization convergence. When constraints are used together with objectives, constraints are always met, while objectives may not necessarily be met (instead, they are goals that the optimizer 212 tries to achieve). In the event of multiple objectives, objectives may be allocated a priority or preference, for example such that a primary objective is considered in a first optimization procedure, a secondary objective is considered in a second optimization procedure following the first optimization procedure, a tertiary objective is considered in a third optimization procedure following the second optimization procedure, and so on.

The cost function 204, together with the model 202, the parameters 206, constraints 208 (optional) and reference objective 210 (optional), may be considered to represent the optimization problem to be solved. The cost function 204, constraints 208, reference objective 210, either alone or in combination, may be referred to as a treatment-planning objective.

The optimizer 212 aims to find a set of optimized parameters 206 for which the cost function 204 is minimised. The optimized parameters 216 are an output of the optimizer 212.

Optionally, the optimizer 212 outputs the cost function value 214. The cost function value 214 is the value of the cost function 204, when evaluated with the optimized parameters 216.

Optionally, the optimizer 212 outputs an achieved goal value 218. The achieved goal value 218 is comparable to the reference objective. An achieved goal value 218 represents a value that has the same units as a given reference objective. The achieved value 218 may be different from the cost function value 214. Unlike the cost function value 214, which may be a number that is an evaluation of the cost function, the achieved value 218 may have a physical meaning. In an example, when the reference objective comprises a dosimetric objective, the achieved goal value also relates to a dose (e.g., it has the units of Gy and/or the same physical meaning as the reference objective). In an example, when the reference objective comprises a reference volume and a dose value, the achieved goal value also relates to a reference volume and a dose value (i.e., it has the same physical meaning as the reference objective). The cost function value 214 may be a number that corresponds to a cost function evaluated with a set of optimized parameters. The achieved goal value 218 would be the achieved percentage of the volume that receives the predetermined dose. In other words, achieved goal value 218 is comparable to the reference objective.

Figure 2B:
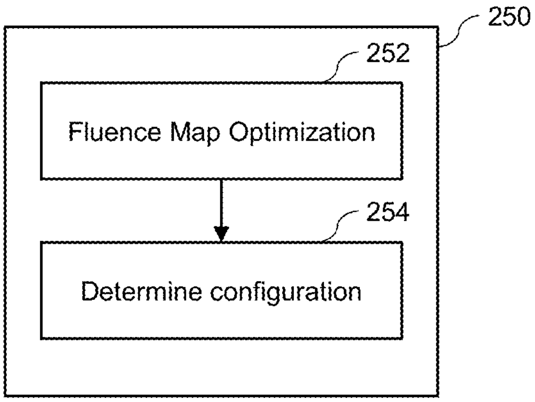
FIG. 2B is an example optimization procedure, for application in intensity-modulated radiation therapy.

FIG. 2B shows an example of a two-stage optimization procedure 250 for IMRT. Although this example applies to IMRT, it is noted that optimization procedure may be applied to other modes of radiotherapy. For instance, the optimization procedure may also be applied to volumetric modulated arc therapy, VMAT.

In IMRT, one or more radiation beams are directed to a tumour (target region). The intensity of each beam profile is non-uniform. The aim of optimization procedure 250 is to modify the intensity profile such that a high enough dose is delivered to the tumour, while reducing the dose delivered to healthy organs (surrounding region).

The method of optimization for IMRT 250 comprises two stages. The first stage 252 is fluence map optimization, FMO, and the second stage 254 is the determination of a configuration of the radiotherapy system. In FMO (stage 252), an optimal fluence map is determined. The optimal fluence map is then used to determine a configuration for the radiotherapy system in the second stage.

For FMO, each beam is divided into a number of beamlets. The contribution of each beamlet, at unit fluence, to voxels is then calculated. During optimization, the weight of each beamlet is adjusted such that a cost function is minimised. By multiplying the weight with the contribution of each beamlet at unit fluence, the full dose distribution may be obtained. The full dose distribution may be compared with any constraints and/or reference objectives to determine if the optimized solution is suitable.

Optimization comprises minimizing a cost function $f(x)$ by determining suitable values of parameters x based on certain constraints g. For FMO, the parameters x correspond to the weight of the beamlets (parameters x may also be referred to as decision variables). The output of FMO (stage 252) comprises parameters x.

The constraints g comprise restrictions. An example of a restriction is a minimum dose at voxels corresponding to a target, or a maximum dose at voxels corresponding to OAR.

In an example, a cost function $f(x)$ is:

$$f(x)=T1+T2+\ldots+T3, \qquad \text{(Eqn. 1)}$$

where, e.g., $T1=\Sigma x_n \cdot d_n$, where, when x corresponds to weight of a beamlet, $d_n$ represents the dose that each beamlet gives to a voxel at unit intensity. $d_n$ is a non-optimizable parameter (e.g., it may depend on machine configuration and/or properties of the tissue). $d_n$ corresponds to the model 202 described above. In an example, the dose $d_n$ may be determined by pencil beam algorithms, convolution based algorithms and/or Monte Carlo (MC) based algorithms. Optionally, dose calculations use pencil beam algorithms or convolution based algorithms (which are fast but have reduced accuracy). Further details of how the dose $d_n$ may be determined are provided in Monaco® Training Guide, Document ID: LTGMON0530 (Elekta AB). The output of stage 1 may include a dose distribution.

In this example, the cost function $f(x)$ is the sum of the total dose (T1, T2, . . . , T3) where each of T1, T2, . . . , T3 represent the dose on different structures. Note that alternative formulations of the problem to be solved (e.g., by defining different cost functions or constraints) may be used.

In an example, the requirement for the dose at a target to be above a certain amount may be formulated as a constraint. Alternatively, such a requirement could be formulated as a reference objective.

Stage 252 provides a set of optimized parameters (e.g., beamlet weights x) that would provide an optimum intensity map (or fluence map). To be ready for delivery by the radiotherapy system, a further stage (stage 153) is required to translate each optimized beamlet weight into a configuration of the machine that would deliver the optimum fluence.

At stage 254, the output from stage 252 is turned into a configuration of a radiotherapy system. The configuration is useable by a radiotherapy apparatus (examples of which are described herein) for delivering radiation therapy. For example, the configuration of the radiotherapy system comprises a set of (i.e., one or more) aperture configurations. The shapes of the aperture configurations may be selected to meet the same goal as in the first stage. Aperture configurations may be realised by a beam shaping apparatus.

An aperture configuration may be referred to as a control point or a segment. The control point and/or segment comprise radiation information (e.g., energy, dose) and geometric information (segment or control point shapes) such as gantry angle and leaf position.

The shapes and weights (i.e., segment or control point weights) of the apertures (segment or control point shapes) may be determined by applying algebraic and trigonometric considerations to the arrangement of the aperture in order to implement the optimized beamlet weights of stage 252.

Alternatively, stage 254 comprises performing a second stage optimization procedure to determine an optimized aperture configuration that would implement the optimized fluence pattern determined in stage 252. The second stage optimization procedure may be referred to as aperture optimization, or aperture refinement.

Aperture optimization may comprise the following:

Receiving a set of beamlet weights (e.g., from stage 252)

Performing optimization to determine optimized aperture shapes. The optimization may be performed using an optimization procedure such as in FIG. 2B, for example. Other optimization procedures are possible.

When the beam shaping apparatus comprises a multi-leaf collimator, MLC, aperture optimization may comprise:

Receiving a set of beamlet weights from FMO and/or fluence profiles (e.g., from stage 252)

Converting the received profile into beamlet widths (the opening between a leaf pair). This results in a segment.

Optimizing the weights of the resulting segments.

Optionally, optimizing shapes of the resulting segments (using a procedure referred to as segment shape optimization).

Note that the optimization steps in stage 254 may comprise a calculation of the dose distribution. The dose distribution may be calculated using pencil beam algorithms, convolution-based algorithms and/or Monte Carlo (MC) based algorithms. Optionally, dose calculations in stage 254 use MC based algorithms (which are more accurate but computationally expensive). Further details of aperture optimization are provided in Monaco® Training Guide, Document ID: LTGMON0530 (Elekta AB).

Note that the procedure of FIG. 2B may relate to one specific angle (radiation beam angle). In an approach, a prior stage may be to determine the angles from which radiation is to be delivered. The beam angle optimization (BAO) procedure may be carried out before the procedure of FIG. 2B and the procedure of FIG. 2B may then be carried out for each determined angle.

While the example of FIG. 2B relates to a two-stage optimization procedure (FMO at stage 252 and determination of a configuration at stage 254) for IMRT, it is noted that alternative methods of optimization, such as Direct Machine Parameter Optimization (DMPO), may be used. In DMPO, the decision variable x corresponds to a parameter of a machine (e.g., an MLC leaf position) that delivers radiation.

Returning to cost function 202 in an optimization procedure, examples of cost functions include: Target EUD, Target Penalty, Quadratic Overdose, Quadratic Underdose, Serial, Parallel, Maximum Dose, Overdose DVH, Underdose DVH. The cost functions are briefly defined below. Each cost function offers different calculation methods. When the cost function comprises any of target penalty, parallel, overdose DVH, and Underdose DVH, the reference objective is a dose value and a relative volume component (e.g., a percentage) or an absolute volume (e.g., in cc).

When the cost function comprises any of Target EUD, quadratic overdose, serial, maximum dose, or conformality, the reference objective is a dose value.

Generally, the optimization procedure seeks to minimize a composite cost-function, comprised of the sum of the cost functions that may be objectives or constraints. A cost function relates an inhomogeneous dose distribution to a single value. One may use this value to define a penalty for violating an objective or constraint. The system may evaluate this penalty value during optimization procedures.

Cost functions such as serial, parallel, quadratic overdose, overdose DVH, or maximum dose aim to limit the dose at an anatomical structure (e.g., a penalty value is imposed if the dose exceeds a threshold). Cost functions such as quadratic underdose or underdose DVH aim to increase the dose at an anatomical structure. Cost functions such as Target EUD and Target Penalty aim to increase the dose at a structure. Some of the above cost functions also take a unitless number as input. The unitless number (k) may be, for example, a power law exponent.

The Target EUD cost function defines a structure as a target volume and expresses the probability that a target cell survives a given dose. This cost function requires a prescribed dose as input (i.e., the reference objective for this cost function is a dose value). The prescribed dose, in Gy, is an equivalent uniform dose (EUD). An EUD is a homogenous dose that, if delivered at an anatomical structure, has the same clinical effect that a non-homogenous dose distribution would provide.

The Target Penalty cost function takes as input a prescribed dose and a minimum volume as input (i.e., the reference objective for this cost function is a dose and a relative volume). The Target Penalty is a quadratic penalty which starts at a threshold dose. It produces steeper dose gradients after a target threshold is met. The Target Penalty is used to define the requirement that at least some fraction of the total anatomical structure volume should receive at least the target dose.

The quadratic overdose (QO) cost function is a cost function used to limit the dose in the structure to which it is applied. The QO may be applied to either targets or OARs. The QO cost function may be used to limit hot spots in a target. The QO cost function takes as input a maximum dose and a root-mean square (RMS) dose excess (i.e., the reference objectives comprise two dose values). The maximum dose defines a dose beyond which a penalty is incurred. The RMS dose excess defines the amount of violation that is acceptable.

The quadratic underdose cost function is a cost function that is applied to a target volume. The quadratic underdose function implements a quadratic penalty. The cost function takes as input a minimum dose in Gy and a dose deficit in Gy (i.e., the reference objective comprises two dose values). The minimum dose is the minimum dose allowable in a target and represents the dose under which a penalty is incurred. The dose deficit is analogous to the RMS dose excess in that it defines the amount of violation from the prescription that is acceptable.

The Serial cost function is generally used with serial OARs. Serial anatomical structures are those where high doses are harmful even if limited to small volumes. Examples include the spinal cord and bowel. This cost function applies large penalties for hot spots even if they are small in volume. The cost function takes as input an EUD in Gy and a power law exponent p (i.e., the reference objective comprises a dose value and a unitless number). An example mathematical formulation of a Serial EUD cost function is as follows:

$$EUD(D; V, \Delta, p, \varepsilon) := \frac{1}{|V|}\sum_{i\in V}\left(\frac{D_i}{\Delta}\right)^p \leq \varepsilon^p \quad \text{(Eqn. 2)}$$

where the cost function represents a summation of i voxels in a volume V of the patient, and where $V_i$ is a volume of an i-th voxel, $D_i$ is a dose delivered to the i-th voxel, $\Delta$ is a reference dose value, the reference dose value being a maximum radiation dose within a target region of the patient and/or a surrounding region of the patient, and $\varepsilon$ is a constant.

The Parallel cost function is generally used for parallel OARs. Parallel structures are those where very high doses in small volumes are tolerated, if the rest of the organ is spared. Examples are lungs, parotids, kidneys, liver. The cost function takes as input a reference dose in Gy, a mean organ damage (which is a fraction of the volume of the structure that may be sacrificed), and power law exponent k (i.e., the reference objective comprises a dose value, a relative volume, and a unitless number).

The Maximum Dose, MXD, cost function is effectively a hard barrier that may be applied to target regions (structures) or surrounding regions (OAR). The Maximum Dose cost function has a penalty that takes effect whenever voxels cross a maximum dose threshold. The cost function takes as input maximum dose in Gy (i.e., the reference objective comprises a dose value). An example mathematical formulation of an MXD cost function is as follows:

$$MXD(D; V, \Delta, \alpha) := \frac{1}{|V|}\sum_{i\in V}|V_i|[D_i - \Delta]_+^4 \leq \alpha \quad \text{(Eqn. 3)}$$

where the cost function represents a summation of i voxels in a volume V of the patient, and where $V_i$ is a volume of an i-th voxel, $D_i$ is a dose delivered to the i-th voxel, $\Delta$ is a reference dose value, the reference dose value being a maximum radiation dose within a target region of the patient and/or a surrounding region of the patient, and $\alpha$ is the maximum dose threshold.

The Overdose DVH cost function takes as input an objective dose in Gy and a maximum volume (i.e., the reference objective comprises a dose value and a relative volume). This cost function is applied to OARs. The purpose is to keep the volume that receives more than the objective dose below the relative volume.

The Underdose DVH cost function takes as input an objective dose in Gy and a minimum volume (i.e., the reference objective comprises a dose value and a relative volume). This cost function is applied to targets. The purpose is to keep the volume of the target that receives less than the objective dose above the minimum volume.

Further details of the cost functions are provided in Monaco® Training Guide, Document ID: LTGMON0530 (Elekta AB).

Figure 3:
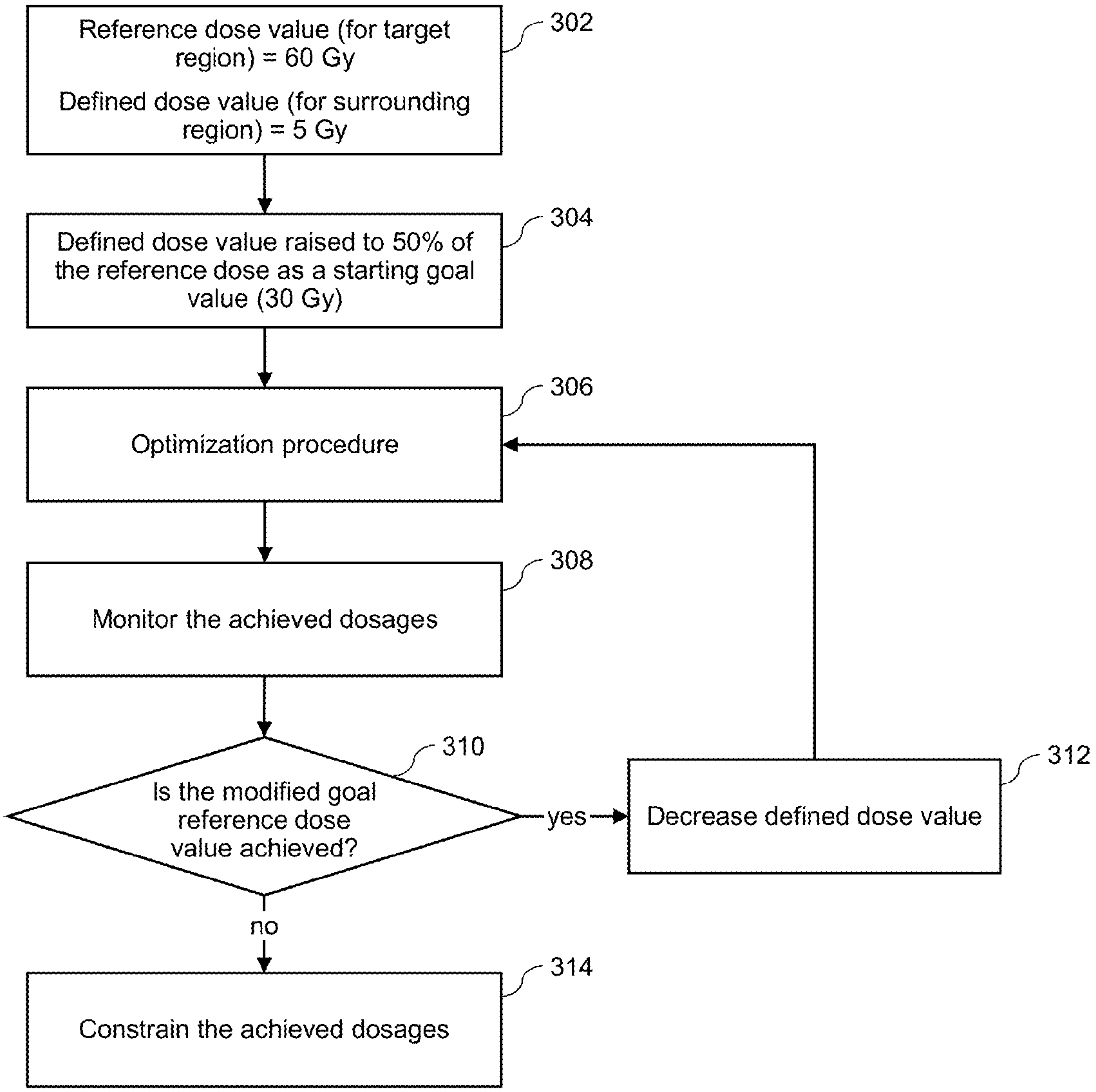
FIG. 3 is a flow chart of a method for radiation treatment planning according to a worked example.

FIG. 3 shows a method for radiation treatment planning, involving iterative adjustment of defined dose value for a surrounding region according to an example. Consider a case of prostate cancer radiation treatment planning. The user may wish for a radiation treatment plan capable of delivering a reference dose of 60 Gy to the prostate while delivering a defined dose value of only 5 Gy to the rectum. The user then inputs these values as treatment plan parameters at step 302.

At step 306, the computer implementing the method then compares the defined dose value to pre-set threshold of 50% of the reference dose (that is, 30 Gy in this case). The computer determines that the defined dose value does not exceed (i.e., is not greater than) the threshold so modifies the defined dose value to obtain a starting point for the optimization procedure. In this case, the computer sets the modified defines dose value to 30 Gy; the skilled reader will appreciate, however, that the threshold and the initial modified dose value need not necessarily be the same. At step 306, the computer begins the optimization procedure, with a view to modifying optimizable parameters and arrive at a dose distribution or dose map that provides a sufficiently high dose to the prostate (ideally, the reference dose value) while reducing the dose to the surrounding healthy tissue of the rectum.

Throughout the optimization procedure (for instance, at the end of one optimization pass, or after a convergence criterion is met), at step 308, the computer monitors the achieved dosages in the prostate and in the rectum.

At step 310, the computer establishes if the achieved dose value in the surrounding region (that is, the dose value associated with the optimizable parameters at their current values) matches the modified dose value of 30 Gy.

If the achieved dose value in the surrounding region, when the optimization procedure reaches its stopping criterion, successfully reaches the modified dose value of 30 Gy, at step 312, the computer decreases the modified dose value and continues the optimization procedure at step 306 with the newly modified dose value (using the previously obtained optimizable parameter values as a starting point for subsequent optimization passes). For instance, the optimization procedure may then seek to achieve a dose value in the surrounding region of 20 Gy.

If the achieved dose value in the surrounding region, when the optimization procedure reaches its stopping criterion, does not successfully reach the modified dose value of 30 Gy, at step 314, the computer constrains the achieved dosages in the prostate and in the rectum. The computer may then proceed to output the optimized parameter values associated with the achieved dosages and any associated radiotherapy system configuration settings suitable for achieving these optimized parameter values and/or dose map.

Figure 4A:
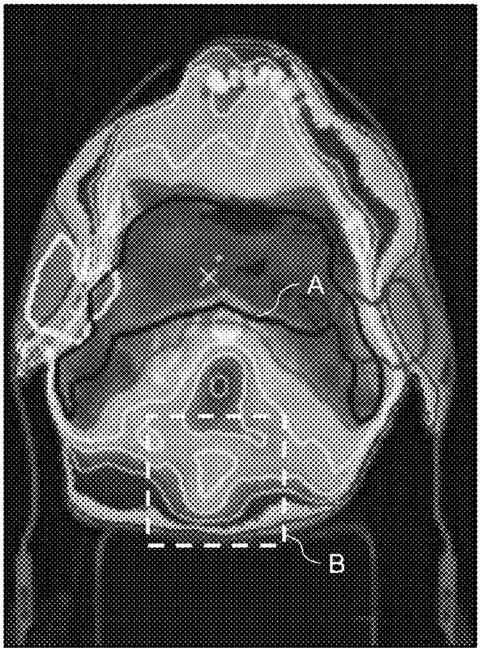
FIG. 4A is an expected dose map, associated with a radiation treatment plan determined according to a conventional procedure.

FIG. 4A is a dose map for a patient, overlaid on a medical image of the patient acquired using a computer tomography, CT, scan. The figure illustrates dose distribution in the form of colour-wash, where different colours represent different doses. Typically, darker colours indicate higher dose, and vice versa. If two locations have exactly same colours, then the doses in these two locations are the same. The figure includes isodose lines, where each of these connected curves displays a certain dose level. Any location at the periphery of a particular curve has the same dose. For example, one isocurve may show dose at 95% of defined dose value, and another isocurve may show dose at 80% of defined dose value.

The dose map is indicative of the expected radiation dosage in accordance with a radiation treatment plan (determined using an optimization procedure), for the treatment of tumours in the oropharynx, while seeking to minimize the dose delivered to the posterior neck. The radiation treatment plan is determined using a conventional procedure. As shown, the target region (bounding the gross and microscopic tumour as well as potentially involved lymph nodes) is the region bound with the line labelled "A". The surrounding region of concern is the area within the region bound with the dashed line labelled "B", which includes the posterior neck. A peak dose value of 49.22 Gy is delivered to the target region. In the surrounding region of concern, an undesired dose of approximately 35 Gy is expected in the central portion.

Figure 4B:
FIG. 4B is an expected dose map, associated with a radiation treatment plan determined according to embodiments.

FIG. 4B is a dose map for the same patient, where the associated radiation treatment plan is determined, instead, using a method according to embodiments. As shown, the expected dosage in the target region (again, bound with the line labelled "A") is largely unchanged; there is only a 4 Gy difference in the mean dose to this region in comparison to the radiation treatment plan determined using a conventional procedure. However, there is a significant decrease in the expected dosage delivered to the surrounding region (region "B").

Figure 5:
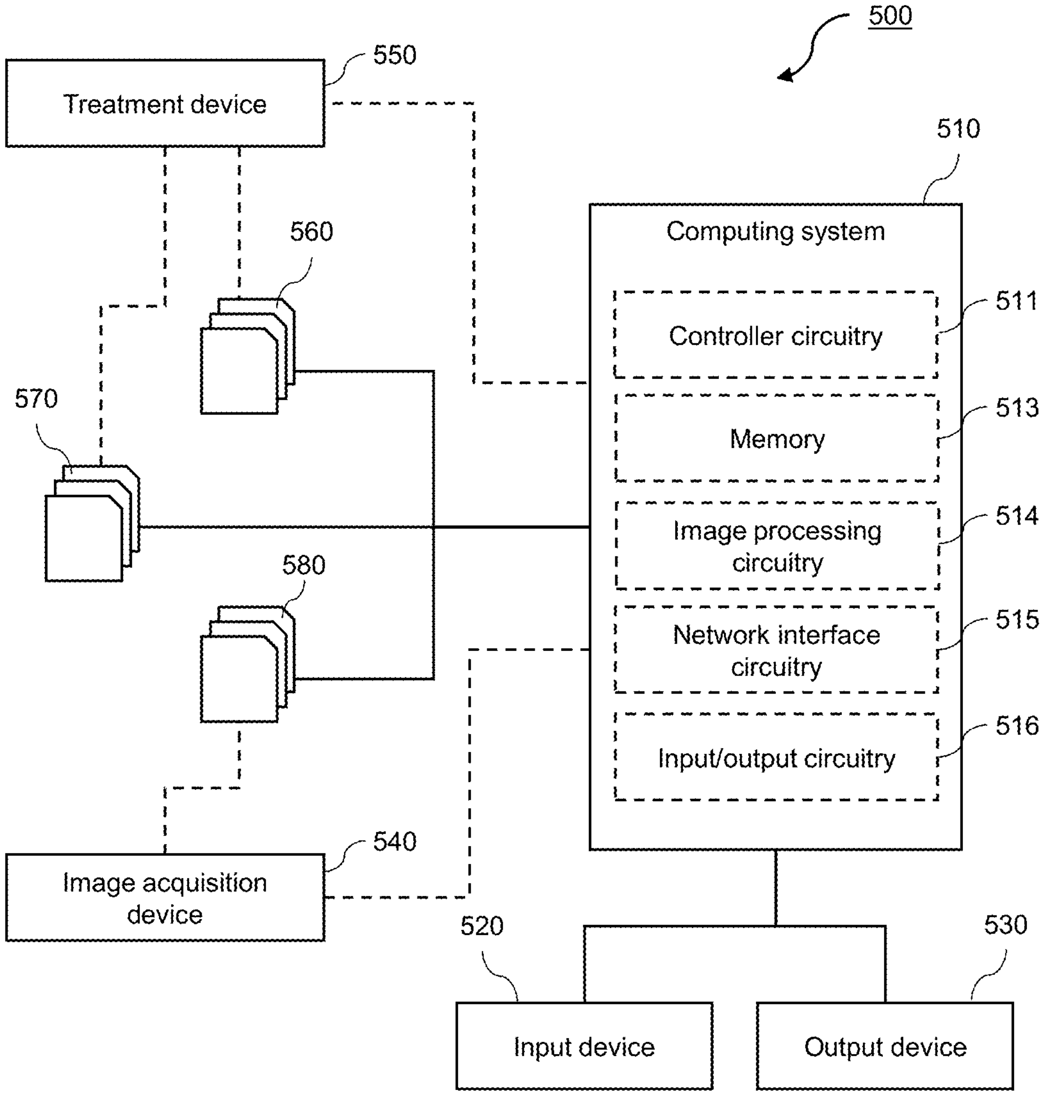
FIG. 5 is a radiotherapy system, suitable for implementing a radiation treatment plan determined according to embodiments.

FIG. 5 is a block diagram of an implementation of a radiotherapy system 500, suitable for executing methods for radiation treatment planning according to embodiments. The example radiotherapy system 500 comprises a computing system 510 within which a set of instructions, for causing the computing system 510 to perform any one or more of the methods (or steps thereof) discussed herein, may be executed. The computing system 510 may implement a treatment planning system. The computing system 510 may also be referred to as a computer. In particular, the methods described herein may be implemented by a processor or controller circuitry 511 of the treatment planning system 510.

The computing system 510 shall be taken to include any number or collection of machines, e.g., computing device(s), that individually or jointly execute a set (or multiple sets) of instructions to perform any one or more of the methods discussed herein. That is, hardware and/or software may be provided in a single computing device, or distributed across a plurality of computing devices in the computing system. In some implementations, one or more elements of the computing system may be connected (e.g., networked) to other machines, for example in a Local Area Network (LAN), an intranet, an extranet, or the Internet. One or more elements of the computing system may operate in the capacity of a server or a client machine in a client-server network environment, or as a peer machine in a peer-to-peer (or distributed) network environment. One or more elements of the computing system may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

The computing system 510 includes controller circuitry 511 and a memory 513 (e.g., read-only memory (ROM), flash memory, dynamic random access memory (DRAM) such as synchronous DRAM (SDRAM) or Rambus DRAM (RDRAM), etc.). The memory 513 may comprise a static memory (e.g., flash memory, static random access memory (SRAM), etc.), and/or a secondary memory (e.g., a data storage device), which communicate with each other via a bus (not shown). Controller circuitry 511 represents one or more general-purpose processors such as a microprocessor, central processing unit, accelerated processing units, or the like. More particularly, the controller circuitry 511 may comprise a complex instruction set computing (CISC) microprocessor, reduced instruction set computing (RISC) microprocessor, very long instruction word (VLIW) microprocessor, processor implementing other instruction sets, or processors implementing a combination of instruction sets. Controller circuitry 511 may also include one or more special-purpose processing devices such as an application specific integrated circuit (ASIC), a field programmable gate array (FPGA), a digital signal processor (DSP), network processor, or the like. One or more processors of the controller circuitry may have a multicore design. Controller circuitry 511 is configured to execute the processing logic for performing the operations and steps discussed herein.

The computing system 510 may further include a network interface circuitry 515. The computing system 510 may be communicatively coupled to an input device 520 and/or an output device 530, via input/output circuitry 516. In some implementations, the input device 520 and/or the output device 530 may be elements of the computing system 510. The input device 520 may include an alphanumeric input device (e.g., a keyboard or touchscreen), a cursor control device (e.g., a mouse or touchscreen), an audio device such as a microphone, and/or a haptic input device. The output device 530 may include an audio device such as a speaker, a video display unit (e.g., a liquid crystal display (LCD) or a cathode ray tube (CRT)), and/or a haptic output device. In some implementations, the input device 520 and the output device 530 may be provided as a single device, or as separate devices.

In some implementations, the computing system 510 may comprise image processing circuitry 514. Image processing circuitry 514 may be configured to process image data 580 (e.g., images, or imaging data), such as medical images obtained from one or more imaging data sources, a treatment device 550 and/or an image acquisition device 540. Image processing circuitry 514 may be configured to process, or pre-process, image data 580. For example, image processing circuitry 514 may convert received image data into a particular format, size, resolution or the like. In some implementations, image processing circuitry 514 may be combined with controller circuitry 511.

In some implementations, the radiotherapy system 500 may further comprise an image acquisition device 540 and/or a treatment device 550. The image acquisition device 540 and the treatment device 550 may be provided as a single device. In some implementations, treatment device 550 is configured to perform imaging, for example in addition to providing treatment and/or during treatment. The treatment device 550 comprises the main radiation delivery components of the radiotherapy system.

Image acquisition device 540 may be configured to perform positron emission tomography (PET), computed tomography (CT), magnetic resonance imaging (MRI), single positron emission computed tomography (SPECT), X-ray, and the like.

Image acquisition device 540 may be configured to output image data 580, which may be accessed by computing system 510. Treatment device 550 may be configured to output treatment data 560, which may be accessed by computing system 510.

Computing system 510 may be configured to access or obtain treatment data 560, planning data 570 and/or image data 580. Treatment data 560 may be obtained from an internal data source (e.g., from memory 513) or from an external data source, such as treatment device 550 or an external database. Planning data 570 may be obtained from memory 513 and/or from an external source, such as a planning database. Planning data 570 may comprise information obtained from one or more of the image acquisition device 540 and the treatment device 550.

The various methods described above may be implemented by a computer program. The computer program may include computer code (e.g., instructions) arranged to instruct a computer to perform the functions of one or more of the various methods described above. For example, the steps of the methods described in relation to FIG. 1, FIG. 2, and/or FIG. 3 may be performed by the computer code. The steps of the methods described above may be performed in any suitable order. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD. The instructions may also reside, completely or at least partially, within the memory 513 and/or within the controller circuitry 511 during execution thereof by the computing system 510, the memory 513 and the controller circuitry 511 also constituting computer-readable storage media.

In an implementation, the modules, components and other features described herein may be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may comprise a special-purpose processor, such as an FPGA or an ASIC. A hardware component may also include programmable logic or circuitry that is temporarily configured by software to perform certain operations.

In addition, the modules and components may be implemented as firmware or functional circuitry within hardware devices. Further, the modules and components may be implemented in any combination of hardware devices and software components, or only in software (e.g., code stored or otherwise embodied in a machine-readable medium or in a transmission medium).

Figure 6:
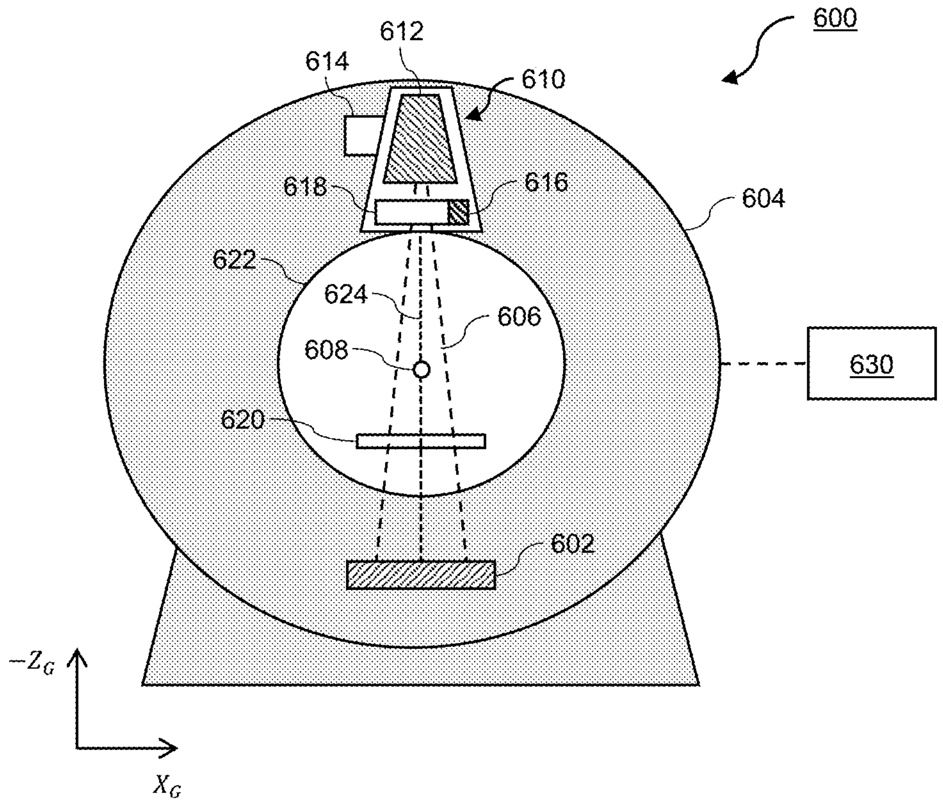
FIG. 6 is a radiotherapy device or apparatus, suitable for implementing a radiation treatment plan determined according to embodiments.

FIG. 6 depicts a radiotherapy apparatus, suitable for implementing radiation treatment plans determined according to embodiments. The cross-section through radiotherapy apparatus 600 includes a radiation head 610 and a beam receiving apparatus 602, both of which are attached to a gantry 604. The radiation head 610 includes a radiation source 612, which emits a beam of radiation 606. The radiation head 610 also includes a beam shaping apparatus 618, which controls the size and shape of the radiation field associated with the beam.

The beam receiving apparatus 602 is configured to receive radiation emitted from the radiation head 610, for the purpose of absorbing and/or measuring the beam of radiation. In the view shown, the radiation head 610 and the beam receiving apparatus 602 are positioned diametrically opposed to one another.

The gantry 604 is rotatable, and supports the radiation head 610 and the beam receiving apparatus 602 such that they are rotatable around an axis of rotation 608, which may coincide with the patient longitudinal axis. The gantry provides rotation of the radiation head 610 and the beam receiving apparatus 602 in a plane perpendicular to the patient longitudinal axis (e.g., a sagittal plane). Three gantry directions $X_G$, $Y_G$, $Z_G$ may be defined, where the $Y_G$ direction is perpendicular with gantry axis of rotation. The $Z_G$ direction extends from a point on the gantry corresponding to the radiation head, towards the axis of rotation of the gantry. Therefore, from the patient frame of reference, the $Z_G$ direction rotates around as the gantry rotates.

Radiotherapy apparatus 600 also includes a support surface 620 on which a subject (or patient) is supported during radiotherapy treatment. The radiation head 610 is configured to rotate around the axis of rotation 608 such that the radiation head 610 directs radiation towards the subject from various angles around the subject in order to spread out the radiation dose received by healthy tissue to a larger region of healthy tissue while building up a prescribed dose of radiation at a target region.

The radiotherapy apparatus 600 is configured to deliver a radiation beam towards a radiation isocentre, which is substantially located on the axis of rotation 608 at the centre of the gantry 604 regardless of the angle at which the radiation head 610 is placed.

The rotatable gantry 604 and radiation head 610 are dimensioned so as to allow a central bore 622 to exist. The central bore 622 provides an opening, sufficient to allow a subject to be positioned therethrough without the possibility of being incidentally contacted by the radiation head 610 or other mechanical components as the gantry rotates the radiation head 610 about the subject.

The radiation head 610 emits the radiation beam 606 along a beam axis 624 (or radiation axis or beam path), where the beam axis 624 is used to define the direction in which the radiation is emitted by the radiation head. The radiation beam 606 is incident on the beam receiving apparatus 602, which may include at least one of a beam stopper and a radiation detector. The beam receiving apparatus 602 is attached to the gantry 604 on a diametrically opposite side to the radiation head 610 to attenuate and/or detect a beam of radiation after the beam has passed through the subject.

The radiation beam axis 624 may be defined as, for example, a centre of the radiation beam 606 or a point of maximum intensity.

The beam shaping apparatus 618 delimits the spread of the radiation beam 606. The beam shaping apparatus 618 is configured to adjust the shape and/or size of a field of radiation produced by the radiation source. The beam shaping apparatus 618 does this by defining an aperture (also referred to as a window or an opening) of variable shape to collimate the radiation beam 606 to a chosen cross-sectional shape. In this example, the beam shaping apparatus 618 may be provided by a combination of a diaphragm and an MLC. Beam shaping apparatus 618 may also be referred to as a beam modifier.

The radiotherapy apparatus 600 may be configured to deliver both coplanar and non-coplanar (also referred to as tilted) modes of radiotherapy treatment. In coplanar treatment, radiation is emitted in a plane which is perpendicular to the axis of rotation of the radiation head 610. In non-coplanar treatment, radiation is emitted at an angle which is not perpendicular to the axis of rotation. In order to deliver coplanar and non-coplanar treatment, the radiation head 610 may move between at least two positions, one in which the radiation is emitted in a plane which is perpendicular to the axis of rotation (coplanar configuration) and one in which radiation is emitted in a plane which is not perpendicular to the axis of rotation (non-coplanar configuration).

In the coplanar configuration, the radiation head is positioned to rotate about a rotation axis and in a first plane. In the non-coplanar configuration, the radiation head is tilted with respect to the first plane such that a field of radiation produced by the radiation head is directed at an oblique angle relative to the first plane and the rotation axis. In the non-coplanar configuration, the radiation head is positioned to rotate in a respective second plane parallel to and displaced from the first plane. The radiation beam is emitted at an oblique angle with respect to the second plane, and therefore as the radiation head rotates the beam sweeps out a cone shape.

The beam receiving apparatus 602 remains in the same place relative to the rotatable gantry when the radiotherapy apparatus is in both the coplanar and non-coplanar modes. Therefore, the beam receiving apparatus 602 is configured to rotate about the rotation axis in the same plane in both coplanar and non-coplanar modes. This may be the same plane as the plane in which the radiation head rotates.

The beam shaping apparatus 610 is configured to reduce the spread of the field of radiation in the non-coplanar configuration in comparison to the coplanar configuration.

The radiotherapy apparatus 600 includes a controller 630, which is programmed to control the radiation source 612, beam receiving apparatus 806 and the gantry 802. Controller 840 may perform functions or operations such as treatment planning, treatment execution, image acquisition, image processing, motion tracking, motion management, and/or other tasks involved in a radiotherapy process.

Controller 630 is programmed to control features of apparatus 600 according to a radiotherapy treatment plan for irradiating a target region, also referred to as a target tissue, of a patient. The treatment plan includes information about a particular dose to be applied to a target tissue, as well as other parameters such as beam angles, dose-histogram-volume information, the number of radiation beams to be used during therapy, the dose per beam, and the like. Controller 630 is programmed to control various components of apparatus 600, such as gantry 604, radiation head 610, beam receiving apparatus 602, and support surface 620, according to the treatment plan. The treatment plan may be determined using methods according to embodiments.

Hardware components of controller 630 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 630 may include operation device software, application software, etc.

The radiation head 610 may be connected to a head actuator 614, which is configured to actuate the radiation head 610, for example between a coplanar configuration and one or more non-coplanar configurations. This may involve translation and rotation of the radiation head 610 relative to the gantry. In some implementations, the head actuator may include a curved rail along which the radiation head 610 may be moved to adjust the position and angle of the radiation head 610. The controller 630 may control the configuration of the radiation head 630 via the head actuator 614.

The beam shaping apparatus 618 includes a shaping actuator 616. The shaping actuator is configured to control the position of one or more elements in the beam shaping apparatus 618 in order to shape the radiation beam 606. In some implementations, the beam shaping apparatus 618 includes an MLC, and the shaping actuator 616 includes means for actuating leaves of the MLC. The beam shaping apparatus 618 may further comprise a diaphragm, and the shaping actuator 616 may include means for actuating blocks of the diaphragm. The controller 630 may control the beam shaping apparatus 618 via the shaping actuator 616.

A treatment plan may comprise positioning information of beam shaping apparatus 618. The positioning information of beam shaping apparatus 618 may comprise information indicating a configuration of one or more elements of beam shaping apparatus 618, such as leaf configuration of an MLC of beam shaping apparatus 618, a configuration of a diaphragm of beam shaping apparatus 618, a configuration of an opening (e.g., window or aperture) of the MLC, and/or the like.

As described herein, the purpose of an optimizer (or of an optimization procedure) is to find a set of optimized parameters for which a cost function is minimised. However, it will be understood that, alternatively and equivalently, the purpose of the optimizer (or of the optimization procedure) may be taken to be to find a set of optimized parameters for which a reward function is maximised.

Unless specifically stated otherwise, as apparent from the following discussion, it is appreciated that throughout the description, discussions utilizing terms such as “receiving”, “determining”, “comparing”, “enabling”, “maintaining,” “identifying,”, “obtaining”, “accessing” or the like, refer to the actions and processes of a computer system, or similar electronic computing device, that manipulates and transforms data represented as physical (electronic) quantities within the computer system’s registers and memories into other data similarly represented as physical quantities within the computer system memories or registers or other such information storage, transmission or display devices.

While certain embodiments have been described, these embodiments have been presented by way of example only, and are not intended to limit the scope of the present disclosure. Indeed, the novel methods and apparatuses described herein may be embodied in a variety of other forms; furthermore, various omissions, substitutions and changes in the form of methods and apparatus described herein may be made.

The following statements may be useful for understanding the present disclosure:

Statement 1: a computer-implemented method for radiation treatment planning, the method comprising: receiving treatment plan parameters including a reference dose value for a target region of a patient and a defined dose value for a surrounding region; determining whether the defined dose value for the surrounding region exceeds a threshold; and responsive to determining that the defined dose value for the surrounding region does not exceed the threshold, modifying the defined dose value for the surrounding region, and applying an optimization procedure to a treatment plan for radiation treatment of the patient with the modified dose value for the surrounding region.

Statement 2: the method of statement 1, wherein the optimization procedure comprises determining a dose distribution indicating expected dosage in the target region and in the surrounding region, based on the reference dose value for the target region and the modified dose value for the surrounding region.

Statement 3: the method of statement 2, wherein the optimization procedure comprises: responsive to determining that the dose distribution indicates that the expected dosage in the surrounding region matches the modified dose value for the surrounding region, adjusting the modified dose value towards the defined dose value; and repeatedly determining the dose distribution until a stopping criterion for the dosage in the surrounding region is reached.

Statement 4: the method of any preceding statement, wherein: the reference dose value for the target region is a minimum dose value for treatment of the target region; and the defined dose value for the surrounding region is a maximum dose value for the surrounding region during treatment of the target region.

Statement 5: the method of any preceding statement, wherein the optimization procedure seeks to minimize a cost function which is representative of dose excess value in the surrounding region and/or the target region.

Statement 6: the method of statement 5, wherein the cost function is a maximum dose, MXD, cost function or a serial cost function.

Statement 7: the method of statement 5 or statement 6, wherein the optimization procedure further seeks to minimize the cost function with respect to one or more optimizable parameters.

Statement 8: the method of statement 5, statement 6, or statement 7, wherein the one or more optimizable parameters comprise one or more of: a dose excess value, beamlets weights, beam angles, dose-histogram-volume information, a number of radiation beams, and a dose per beam.

Statement 9: the method of any preceding statement, wherein the treatment plan parameters include defined dose values for a plurality of surrounding regions, and the method comprises: for each defined dose value for a surrounding region, determining whether the defined dose value for the surrounding region exceeds a threshold; and for each defined dose value for a surrounding region, responsive to determining that the defined dose value for the surrounding region does not exceed the threshold, modifying the defined dose value for the surrounding region, and applying the optimization procedure to the treatment plan for radiation treatment of the patient with the modified dose value for the surrounding region.

Statement 10: the method of any preceding statement, wherein the treatment plan parameters include reference dose values for a plurality of target regions, and the method comprises: for each reference dose value for a target region, determining whether the defined dose value for the surrounding region exceeds a threshold; and for each dose value for a target region, responsive to determining that the defined dose value for the surrounding region does not exceed the threshold, modifying the defined dose value for the surrounding region, and applying the optimization procedure to the treatment plan for radiation treatment plan of the patient with the modified dose value for the surrounding region.

Statement 11: the method of any preceding statement, wherein the threshold is a function of the dose value for the target region.

Statement 12: the method of any preceding statement, wherein the threshold is selected from amongst a plurality of thresholds, each threshold being associated with a corresponding cost function used for the optimization procedure.

Statement 13: the method of any preceding statement, wherein the treatment plan parameters include at least one medical image of a patient comprising the target region and the surrounding region.

Statement 14: the method of any preceding statement, further comprising accepting user input into a graphical user interface, the user input comprising the dose value for the target region and the defined dose value for the surrounding region.

Statement 15: the method of any preceding statement, further comprising outputting parameter values corresponding to the treatment plan, wherein the parameter values comprise one or more of: a dose excess value, beamlet weights, beam angles, dose-histogram-volume information, a number of radiation beams, and a dose per beam.

Statement 16: a data processing apparatus comprising: a memory storing computer-executable instructions; and a processor configured to execute the instructions to carry out the method of any of statements 1 to 15.

Statement 17: a computer program comprising instructions which, when the program is executed by a computer, cause the computer to carry out the method of any of statements 1 to 15.

Statement 18: a non-transitory computer-readable storage medium comprising instructions which, when executed by a computer, cause the computer to carry out the method of any of statements 1 to 15.

What is claimed is:

1. A computer-implemented method for radiation treatment planning, the method comprising:

receiving one or more treatment plan parameters including a reference dose value for a target region of a patient and a defined dose value for a surrounding region;

determining whether the defined dose value for the surrounding region exceeds a threshold; and responsive to determining that the defined dose value for the surrounding region does not exceed the threshold, increasing the defined dose value for the surrounding region to the threshold, and applying an optimization procedure to a treatment plan for radiation treatment of the patient with the increased dose value for the surrounding region.

2. The method of claim 1, wherein the optimization procedure comprises:

determining a dose distribution indicating expected dosage in the target region and in the surrounding region, based on the reference dose value for the target region and the increased dose value for the surrounding region.

3. The method of claim 2, wherein the optimization procedure comprises:

responsive to determining that the dose distribution indicates that the expected dosage in the surrounding region matches the increased dose value for the surrounding region, adjusting the increased dose value towards the defined dose value; and repeatedly determining the dose distribution until a stopping criterion for the dosage in the surrounding region is reached.

4. The method of claim 1, wherein:

the reference dose value for the target region is a minimum dose value for treatment of the target region; and the defined dose value for the surrounding region is a maximum dose value for the surrounding region during treatment of the target region.

5. The method of claim 1, wherein the optimization procedure reduces a cost function which is representative of dose excess value in the surrounding region and/or the target region.

6. The method of claim 5, wherein the cost function is a maximum dose, (MXD), cost function or a serial cost function.

7. The method of claim 5, wherein the cost function is a serial cost function.

8. The method of claim 5, wherein the optimization procedure further reduces the cost function with respect to one or more optimizable parameters.

9. The method of claim 8, wherein the one or more treatment plan parameters comprise one or more of: a number of beams, one or more beam angles, a dose per beam, beamlet weights, one or more segment or control point shapes, one or more segment or control point weights, a dose-volume histogram information, or a dose excess value.

10. The method of claim 1, wherein the one or more treatment plan parameters include defined one or more dose values for a plurality of surrounding regions, and the method comprises:

for each defined dose value for a surrounding region, determining whether the defined dose value for the surrounding region exceeds a threshold; and for each defined dose value for a surrounding region, responsive to determining that the defined dose value for the surrounding region does not exceed the threshold, increasing the defined dose value for the surrounding region, and applying the optimization procedure to the treatment plan for radiation treatment of the patient with the increased dose value for the surrounding region.

11. The method of claim 1, wherein the treatment plan parameters include one or more reference dose values for a plurality of target regions, and the method comprises:

for each reference dose value for a target region, determining whether the defined dose value for the surrounding region exceeds a threshold; and for each dose value for a target region, responsive to determining that the defined dose value for the surrounding region does not exceed the threshold, increasing the defined dose value for the surrounding region, and applying the optimization procedure to the treatment plan for radiation treatment plan of the patient with the increased dose value for the surrounding region.

12. The method of claim 1, wherein the threshold is a function of the dose value for the target region.

13. The method of claim 1, wherein the threshold is selected from amongst a plurality of thresholds, each threshold being associated with a corresponding cost function used for the optimization procedure.

14. The method of claim 1, wherein the one or more treatment plan parameters include at least one medical image of a patient comprising the target region and the surrounding region.

15. The method of claim 1, further comprising:

accepting user input into a graphical user interface, the user input comprising the dose value for the target region and the defined dose value for the surrounding region.

16. The method of claim 1, further comprising:

outputting one or more parameter values corresponding to the treatment plan, wherein the parameter values comprise one or more of: a number of beams, one or more beam angles, a dose per beam, one or more beamlet weights, one or more segment or control point shapes, one or more segment or control point weights, a dose-volume histogram information, or a dose excess value.

17. A data processing apparatus comprising:

a memory storing computer-executable instructions; and a processor configured to execute the instructions to:

receive one or more treatment plan parameters including a reference dose value for a target region of a patient and a defined dose value for a surrounding region;

determine whether the defined dose value for the surrounding region exceeds a threshold; and responsive to determining that the defined dose value for the surrounding region does not exceed the threshold, increase the defined dose value for the surrounding region to the threshold, and apply an optimization procedure to a treatment plan for radiation treatment of the patient with the increased dose value for the surrounding region.

18. A non-transitory computer-readable storage medium comprising instructions which, when executed by a computer, cause the computer to:

receive one or more treatment plan parameters including a reference dose value for a target region of a patient and a defined dose value for a surrounding region;

determine whether the defined dose value for the surrounding region exceeds a threshold; and responsive to determining that the defined dose value for the surrounding region does not exceed the threshold, increase the defined dose value for the surrounding region to the threshold, and apply an optimization procedure to a treatment plan for radiation treatment of the patient with the increased dose value for the surrounding region.

19. A computer-implemented method for radiation treatment planning, the method comprising:

receiving one or more treatment plan parameters including a reference dose value for a target region of a patient and a defined dose value for a surrounding region;

determining whether the defined dose value for the surrounding region exceeds a threshold; and responsive to determining that the defined dose value for the surrounding region does not exceed the threshold, modifying the defined dose value for the surrounding region, and applying an optimization procedure to a treatment plan for radiation treatment of the patient with the modified dose value for the surrounding region, wherein the optimization procedure reduces a serial cost function which is representative of dose excess value in the surrounding region and/or the target region.

* * * * *